United States Patent
Blasing et al.

(10) Patent No.: US 6,323,477 B1
(45) Date of Patent: Nov. 27, 2001

(54) METHOD FOR DETECTING OBJECTS LOCATED ON A TRANSPARENT PANEL, AND CORRESPONDING DEVICE

(75) Inventors: Frank Blasing, Werl; Norbert Bendicks, Hemer, both of (DE)

(73) Assignee: Leopold Kostal GmbH & Co. KG, Ludenscheid (DE)

( * ) Notice: Subject to any disclaimer, the term of this patent is extended or adjusted under 35 U.S.C. 154(b) by 0 days.

(21) Appl. No.: 09/555,532
(22) PCT Filed: Jan. 16, 1999
(86) PCT No.: PCT/EP99/00229
§ 371 Date: May 30, 2000
§ 102(e) Date: May 30, 2000
(87) PCT Pub. No.: WO99/38737
PCT Pub. Date: Aug. 5, 1999

(30) Foreign Application Priority Data

Jan. 30, 1998 (DE) .............................................. 198 03 694

(51) Int. Cl.[7] .................................................. H01L 27/00
(52) U.S. Cl. ......................................... 250/208.1; 250/574
(58) Field of Search .............................. 250/208.1, 208.2, 250/574, 227.25, 214 AL, 341.8, 573; 340/602

(56) References Cited

U.S. PATENT DOCUMENTS 6,084,519 * 7/2000 Coulling et al. ..................... 340/602

6,144,022 * 11/2000 Tenenbaum et al. ............. 250/208.1

\* cited by examiner

*Primary Examiner*—David V. Bruce
*Assistant Examiner*—Hoon K. Song
(74) *Attorney, Agent, or Firm*—Brooks & Kushman P.C.

(57) ABSTRACT

The invention relates to a method for detecting objects which are located on a transparent panel and which produce light reflexes when illuminated, using a detector unit containing one or more optical sensor arrays. The inventive method comprises the following steps: illuminating the panel in order to produce light reflexes in or on the objects which are located on the panel, from the side of the panel behind which the detector unit is located; image detection of an illuminated section of the panel using the detector unit by preparing two panel section images which together form an image pair, the light reflexes(es) of an object located on the transparent panel produced through illumination being located at differently-positioned image points in each of said panel section images; determining the differential image of the two images of an image pair by subtracting the contents of identically positioned image points of one panel section image from those of the other panel section image and evaluating the differential image determined in terms of the contents corresponding to the individual image points.

13 Claims, 3 Drawing Sheets

METHOD FOR DETECTING OBJECTS LOCATED ON A TRANSPARENT PANEL, AND CORRESPONDING DEVICE

TECHNICAL FIELD

The invention pertains to the field of recognition of objects on a transparent pane, perhaps a windshield of a motor vehicle. In particular, the invention pertains to a method for detecting objects present on a transparent pane using a pickup unit containing an optical sensor array. The invention additionally pertains to a device for detecting illuminated objects present on a transparent pane, a pickup unit with an optical sensor array for detecting light beams emitted from an illumination apparatus and reflected, as well as an evaluation unit.

BACKGROUND ART

Such a method is employed, for instance, for detecting raindrops present on the windshield of a motor vehicle to control a wiper motor. Such a device is accordingly referred to as a rain sensor. Such a method as well as such a rain sensor is known from U.S. Pat. No. 4,867,561. The detection method described in this document operates according to the reflection principle, utilizing total reflection on the outside of the windshield. To this end, the rain sensor comprises an infrared diode (IR diode) constructed as an illumination apparatus, the emitted beams of which are directed from the inside onto a section of the windshield to be observed. As a pickup unit, an optical sensor array which is preceded by a lens for imaging [light from] the IR diode onto its photosensitive surface is used. The illumination apparatus and the pickup unit are positioned with respect to one another such that light beams emitted from the light-emitting diode that are reflected by total reflection of the windshield are imaged onto the sensor array in case of a clean windshield. The previously known method uses the fact that said total reflection of the light beams emitted from the illumination apparatus occurs from the outside of the windshield to the sensor array in case of the absence of objects on the windshield. On the other hand, if raindrops are present on the outside of the windshield, light beams are output coupled by the raindrops, so that only a part of the light beams is reflected to the sensor array. Consequently, the light intensity that can be detected by the sensor array in case of the presence of objects on the windshield is lower compared to the light intensity detected for total reflection.

The signals of the sensor array are first filtered in an evaluation unit downstream of the sensor array in order that those signal components which cannot be associated with the light beams emitted from the illumination apparatus are not further evaluated. To this end, the filtering is designed to be wavelength-specific. The filtered sensor array output signal is then fed to a comparator element in which a threshold value comparison of the detected light intensity to a specified threshold value is performed. If the detected light intensity is lower than the threshold value, a control signal, which is applied to a microcomputer for triggering the wiper motor, is present at the output of the comparator element.

Even if the method or device described in this document permits an improved detection over and against older ones, the method is nonetheless subject to error influences. Sunbeams or other light beams refracted on the windshield, whose refraction also produces infrared components which can then impinge on the sensor array, can be considered interfering factors. Since the evaluation of the light intensity detected in the sensor array is adapted by specification of the threshold value to the emitted light intensity of the illumination apparatus, such secondary influences can superimpose the output coupling of light beams by raindrops adhering to the windshield, so that the resulting evaluation outcome no longer corresponds to the actual conditions.

Furthermore, the previously known method is not suited to detect objects on the windshield for which an output coupling of light beams does not occur, such as dust or the like.

SUMMARY OF THE INVENTION

Starting from the prior art as just discussed, the problem of the invention is, first of all, to propose a method for detecting objects present on a transparent pane with which a more exact detection of objects present on the windshield is guaranteed, with simultaneous suppression of irrelevant light signals or interfering influences. The invention is also based on the problem of providing a corresponding device.

The problem related to the method is solved according to the invention by a method for detecting objects present on a transparent pane that produce reflections of light when illuminated, said method using an analysis unit containing one or more optical sensor arrays and comprising the following steps:

illumination of the pane to generate light reflections in or on objects present on the pane from that side of the pane behind which the pickup unit is arranged;

imaging detection of an illuminated pane section with the pickup unit by provision of two pane section images forming an image pair, in which two pictures the light reflection or reflections of an object present on the pane are respectively located at pixels with different positions;

acquisition of the difference image of the two images of an image pair by subtraction of the contents of pixels of equal position on the one pane section image from those of the other pane section image and subsequent analysis of the acquired difference image with respect to the contents associated with the individual pixels.

The device-related problem is solved, first of all, in that as a pickup unit a single sensor array is provided in an arrangement with respect to the pane such that the surface of the pane section detected by the sensor array which is to be observed lies in the depth of focus range of the imaging system depicting the pane section on the photosensitive surface of the sensor array and in that the illumination apparatus comprises at least two mutually separated light sources illuminating the pane section observed by the pickup unit from different directions.

The device-related problem is additionally solved in that the pickup unit comprises two mutually separated optical sensor arrays in a stereoscopic arrangement with respect to the pane in which the surface to be observed of the pane section detected by the sensor array lies in the depth of focus range of the imaging system depicting the pane section on the photosensitive surface of the sensor array, which optical sensor array for observing a pane section is arranged such that the background located a given distance from the pane to be observed is imaged on the two sensor arrays at pixels with the same position.

According to the proposed method, an analysis of the observed pane section takes place not only on the basis of a single image of on the basis of the contents of its pixels, but on the basis of two individual images, each referred to in these writings as a pane section image and jointly as an image pair. It is also provided that the same pane section can be reproduced with the two pane section images, but that the light reflections produced by the illumination of an object located on the pane are imaged in each pane section image at pixels with different positions, or only on one pane section image. Influences that can be traced back to light reflections not generated by the illumination from the objects present on the pane, on the other hand, are imaged at identical points in the two pane section images. The illumination of the pane section to be detected can be done by available ambient light (daylight) or by an additional illumination apparatus. In the subsequent stage of ascertaining the difference image from the two pane section images, the contents of pixels with the same positions are subtracted from one another. Ultimately this leads to a difference image in which the contents of those pixels which are the result of the subtraction of pixels with the same position have the value 0. On the other hand, those pixels whose contents are different—due perhaps to the detection of light reflections of differing positions—receive a value different from 0, possibly the value 1. Since interference influences as a rule appear from the background, they are imaged onto both pane sections at pixels with the same position and are thus eliminated by acquiring the difference image. Consequently, only those signals which are associated with objects adhering to the panes are subjected to the subsequent analysis.

The two pane section images can, for instance, be prepared by being recorded by one and the same optical sensor array in temporal succession where, however, each pane section image is recorded at a different illumination configuration with respect to the direction of incidence of the light beams from an illumination apparatus impinging on the pane. In such a configuration, the pane section image of an image pair which is recorded first is stored in an image memory, until the second pane section image of the image pair has been recorded. Additionally, the two pane section images can be recorded by using a stereoscopic sensor array arrangement. This stereoscopic sensor array arrangement is oriented such that, starting from a certain distance from it, the background detected by the sensor array arrangement is imaged onto pixels with the same position. As a distance in this regard, it is possible, for instance, to assume the distance of the windshield from the front edge of the engine hood. It is practical for the two pane section images to be recorded simultaneously with both sensor arrays. This sensor array arrangement can also operate without an active illumination apparatus in case of sufficient ambient light. If the ambient light is not sufficient, then it is provided for a shared illumination apparatus to be associated with this stereoscopic sensor arrangement in order to illuminate the pane or the objects on it which are to be detected. With this arrangement, it is not necessary that the same pane section always be observed, so long as the above-stated requirement regarding the imaging of the background is satisfied.

With the above-described device it is possible for either the outer pane surface or the inner pane surface or both pane surfaces to be observed, depending on the depth of field selected.

An analysis of the acquired difference image can be done, for instance, by way of an estimation of the energy by a differential image energy determination, as is described in German Patent Application No. 197 36 584.1 by the applicant, which method is hereby incorporated into this description by reference.

An analysis of the acquired difference image can also be performed in regard to the dark/light transitions (edges) contained in it. In such an analysis, it is practical if the analysis method includes a processing of the difference image with an edge operator, in which edge operation an edge enhancement is achieved with a simultaneous suppression of an identical surface. In principle, for instance, a gradient formation, a differentiation or a use of stochastic operators can be employed as the edge operation, with the use of stochastic operators being preferred.

To eliminate an undesired impulse noise, the difference image can be subsequently median-filtered. For further processing of the difference image and further elimination of possible residual interfering influences, the analysis of the acquired difference image can additionally comprise a time-domain low-pass filtering. The assumption in such a low-pass filtering is that objects on the pane to be detected can be captured over several image sequences or periods at identical pixels. In this filtering, therefore, glare or reflections that are caused by scratches in the windshield and are contained only in individual image sequences are eliminated.

In an additional step, the analysis of the difference image can comprise the preparation of a binary image file from the image points of the acquired and processed difference image so that ultimately either the value 0 or the value 1 is assigned to every pixel of the difference image. The generation of the binary image file is done by comparison of the pixel contents to a predetermined threshold value. This step can be followed by a total-image energy calculation, in which the values of all pixels are added up to obtain information on the number of edges or light/dark transitions (=light reflections detected). In such a comparator step there is a comparison of the total image energy to a constant or adaptive threshold value in a comparator element which, in case the threshold value is exceeded, emits a signal for triggering an actor, for instance, a wiper motor.

Alongside the aforementioned analysis by a total-image energy calculation, there can also be an analysis by cluster formation of adjacent pixels with the value 1. The clustering generated can then be analyzed with the aid of the customary statistical methods. Particularly preferred is an analysis method in which the result of the statistical cluster analysis is used to adjust the threshold required for the performance of the comparator step following the total energy calculation. Thus, the threshold value of the comparator element can be adapted to the magnitude of the detected objects.

Additional advantages of the invention result from the addition subordinate claims as well as from the description of figures below. Shown are:

BEST MODES FOR CARRYING OUT THE INVENTION

Figure 1:
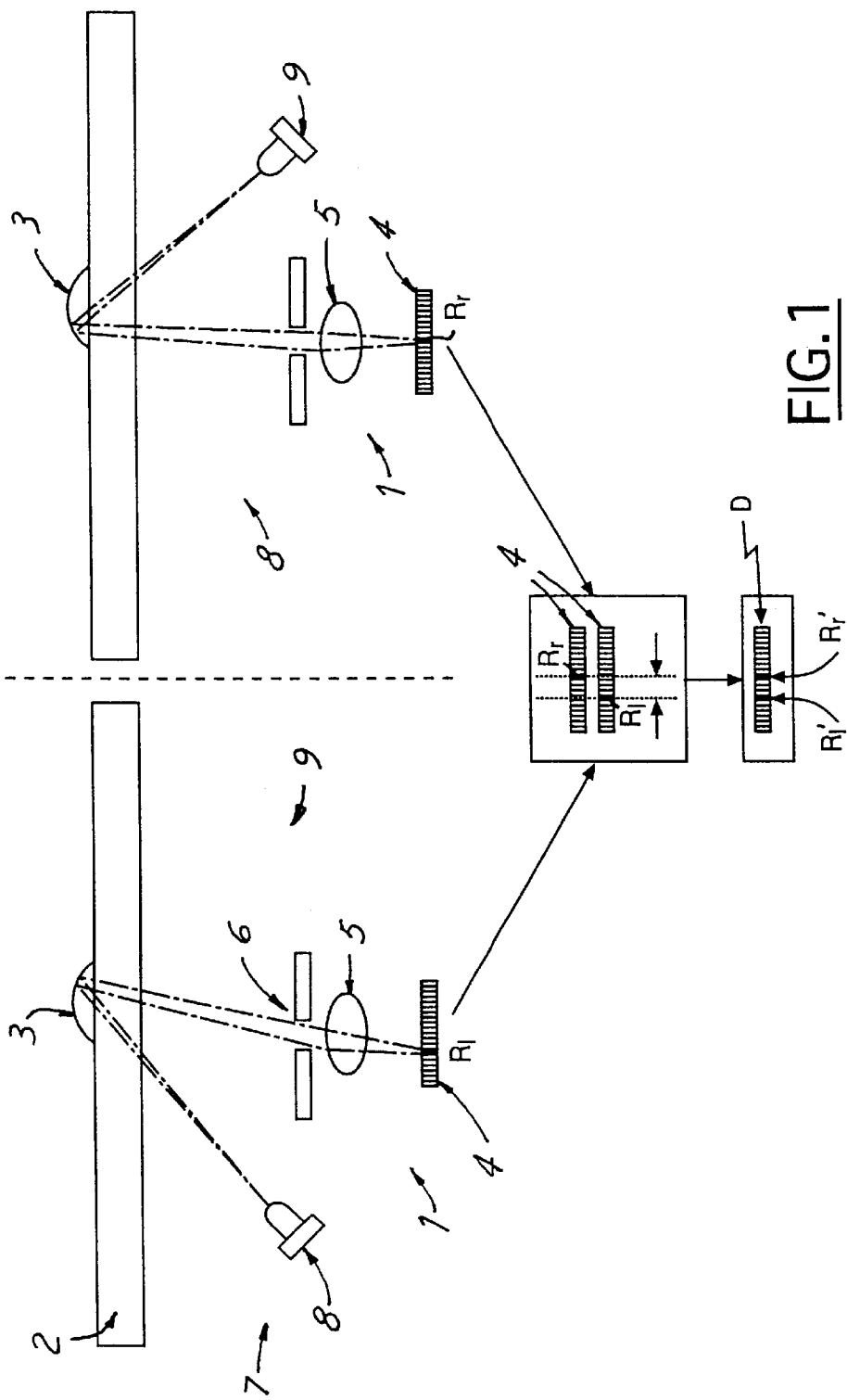
FIG. 1, a schematic representation of a device for detecting objects present on a transparent pane, using a single optical sensor array.

As shown in FIG. 1, the recording unit 1 for detecting raindrops 3 present on a transparent pane, here a windshield 2, comprises an optical line sensor 4, possibly a CCD line, a convex lens 5 inserted in front of the line sensor 4, as well as a perforated diaphragm 6. The recording unit 1 is focused onto the outside of the windshield 2, the depth of focus range of the windshield section imaged onto the photosensitive surface of the line sensor 4 likewise comprising areas slightly above the outer surface of the windshield 2 as well as in the vicinity of the inside surface of the windshield 2, due to the perforated diaphragm 6. To produce light reflections in the raindrops 3 adhering to the windshield 2, an illumination apparatus 7 is provided, consisting in the illustrated embodiment of two IR diodes 8, 9.

To prepare two pane section images in which the light reflection of the raindrop 3 on the windshield 2 produced by the illumination apparatus 7 is located at pixels with different positions, a first pane section image is recorded with an illumination of the raindrop 3 solely by the IR diode 8. This situation is presented in the left half of FIG. 1 under the title "Illumination from the left." The reflection $R_l$ produced in the raindrop 3 by the reflection of light beams emitted by the light-emitting diode 8 is detected with the necessary imaging sharpness by the line sensor 4 or by some of its pixels. A second pane section image is subsequently recorded with an illumination of the windshield 2 by the light-emitting diode 9, so that the light reflection $R_r$ produced by this illumination can be recorded with sufficient imaging sharpness by the line sensor 4 or by some of its pixels. This recording situation is presented in the right half of FIG. 1 under the title "Illumination from the right."

The two IR diodes 8, 9 are placed, as is evident from FIG. 1, such that their emitted light beams illuminate the windshield 2 from different angles of incidence and produce a light reflection $R_l$ or $R_r$ at corresponding different positions in the raindrop 3. Therefore, the light reflections $R_l$, $R_r$, produced by the raindrop 3 are imaged, at least in part, on different pixels of the line sensor 4. For the sake of illustration, the sensor lines with the respective images $R_l$, $R_r$ are shown one above the other in the lower part of FIG. 1, as synonyms for the recorded pane section images. If, in a first processing step, a difference image is generated from the two pane section images, a virtual difference image results of the type shown schematically and labeled D. For this difference image D, pixels of the lower pane section image with an illumination from the left have been subtracted from those of the pane section image recorded with an illumination from the right. Pixels in the same position having the same content thus receive the value 0 and are presented black in the difference image D. Differences in absolute value between pixels of the same position are accordingly presented as illuminated pixels in the difference image D. Since the light reflections $R_l$, $R_r$ detected in the two pane section images partially overlap in the embodiment shown, this area is also black in the difference image D. The result of this difference image acquisition thus represents the two light reflections $R_l$, $R_r$ or their light reflection components $R_{l'}$, $R_{r'}$.

By the provision of the two pane section images with different angles of illumination incidence, it becomes recognizable that light reflections naturally can be recorded by the recording unit 1 only if objects, for instance, raindrops 3, are actually adhering to the windshield 2. If, on the other hand, there are no objects on the windshield 2, the same background is detected in the two pane section images recorded in temporal sequence, so that after a difference formation, the pixel contents of the difference image all have the value 0. Light reflections possibly produced in the background by the illumination that are detected by the recording unit 1 will, first of all, have only a very low light intensity because of their much greater distance [from the sensor] compared to the distance of the windshield 2; moreover, they will be imaged onto pixels of identical position.

Figure 2:
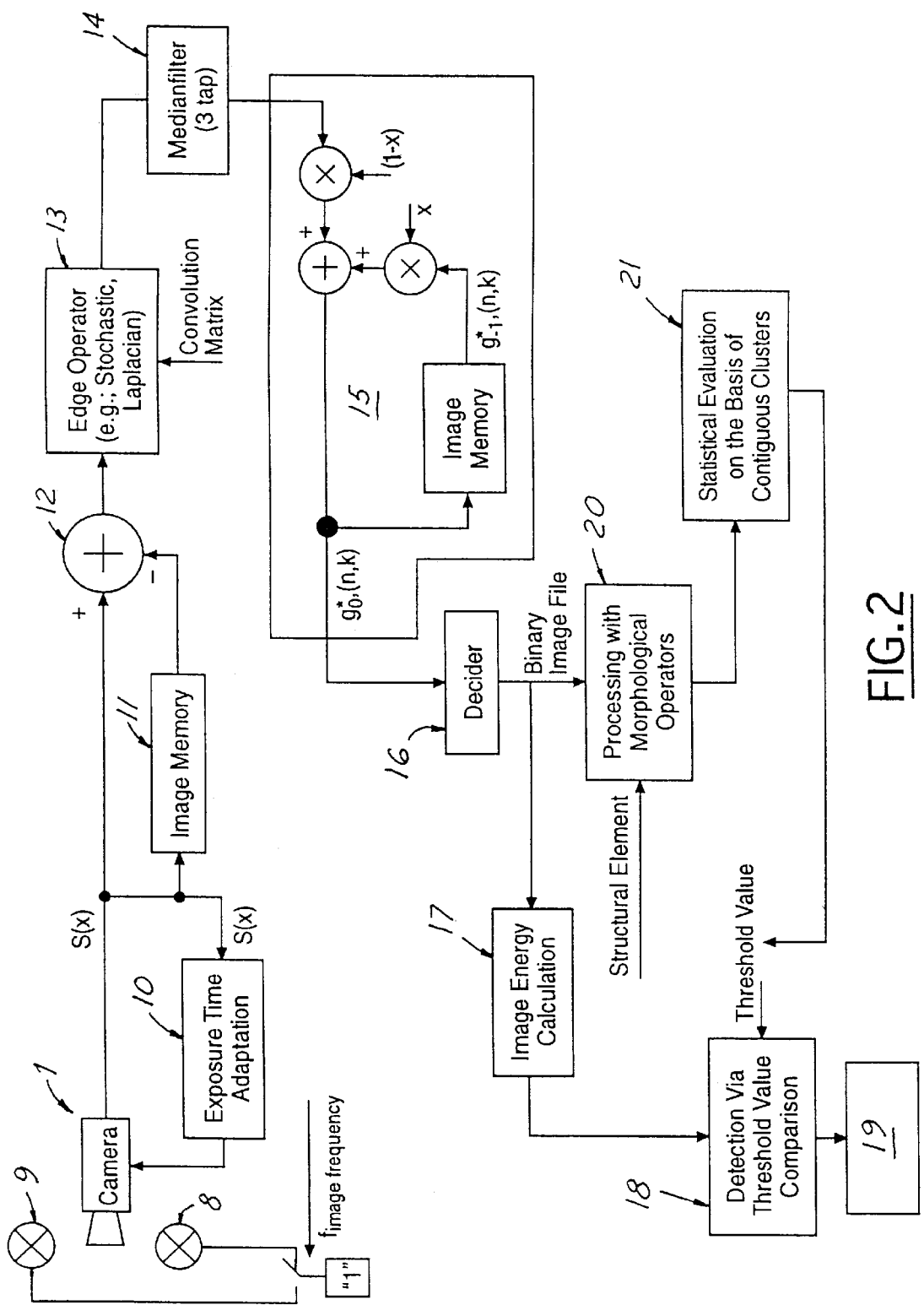
FIG. 2, a schematized block circuit diagram representing a method for detecting objects present on a transparent pane.

In the block circuit diagram schematically presented in FIG. 2 it is recognizable that the recording unit 1 is controlled in its exposure time by a device 10 for exposure time adaptation. Corresponding to the alternate triggering of the IR diode 8 and the IR diode 9, a respective pane section image is recorded in the recording unit 1. The first-recorded pane section image of an image pair to be processed is stored in an image memory 11 and then retrieved again from it when the second pane section image has been recorded by the recording unit 1. The two pane section images of an image pair are subsequently applied to an difference image computer 12, in which the difference image D is determined on the basis of the two pane section images in the above-described manner.

The difference image D, or the information contained in the pixels of the difference image D, is subsequently analyzed. In a first analysis step, an edge operation is performed in an edge operator element 13, through which edge operation an edge enhancement or an enhancement of the light/dark transitions of the difference image D is performed with a simultaneous suppression of the identical surfaces. Stochastic operators are preferably used as the edge operator.

Following the edge operation, the difference image is filtered in a median filter 14 to suppress any impulse noise that may be present. In the illustrated embodiment the filter length amounts to three pixels; naturally other suitable filter lengths can be provided. The median-filtered difference image is low-pass-filtered by a low-pass filter 15 in an additional analysis step, so that after this filtering, values are not equal to 0 in those pixels of the difference image that were detected over a predetermined number of image periods. Thus, glare that is produced by approaching vehicles or by scratches in the windshield, and hence is present only in individual image periods, is filtered out by the low-pass filter 15.

The filtered difference image is subsequently applied to a decider element 16, in which a binary image file is generated from the difference image present on the input side, so that each pixel of the difference image processed up to this step has either the value 0 or the value 1. This function of the decider 16 is achieved by applying a predetermined threshold value to it.

The additional image processing is performed in two processing branches—an image energy calculation with subsequent threshold value comparison, as well as a clustering with subsequent statistical evaluation. The image energy calculation is done in an image energy calculation element 17, in which the number of pixels whose value is 1 in the differential image present as a binary file is determined. Depending on the illumination apparatus, specifically, depending on the number of illumination means used for each pane section image, information can be obtained on the actual number of raindrops detected on the windshield 2. This value is applied to a comparator element 18 whose output is present at the input of a microprocessor 19 for triggering actors not shown in detail, such as a wiper motor. A threshold value, which is adjustable according to the illustrated embodiment, is applied to the comparator element 18.

For further analysis of the number of reflections determined in the image energy calculation, there is first of all a position-dependent clustering of those pixel contents whose value is 1. According to the predetermined cluster conditions, those pixels which meet the cluster conditions are brought together as a cluster. This processing takes place in a cluster element 20. Connected on the output side to the cluster element 20 is a statistical evaluation element 21, in which the number of clusters formed is statistically analyzed. As the result, an evaluation of the size of the detected raindrops is possible. In the illustrated embodiment, the result of the statistical evaluation is employed for the adaptation of the threshold value applied to the comparator 19. Thus a direct feedback of morphologically varying properties of the detected objects takes place with regard to a triggering of the actors adapted to them.

Figure 3:
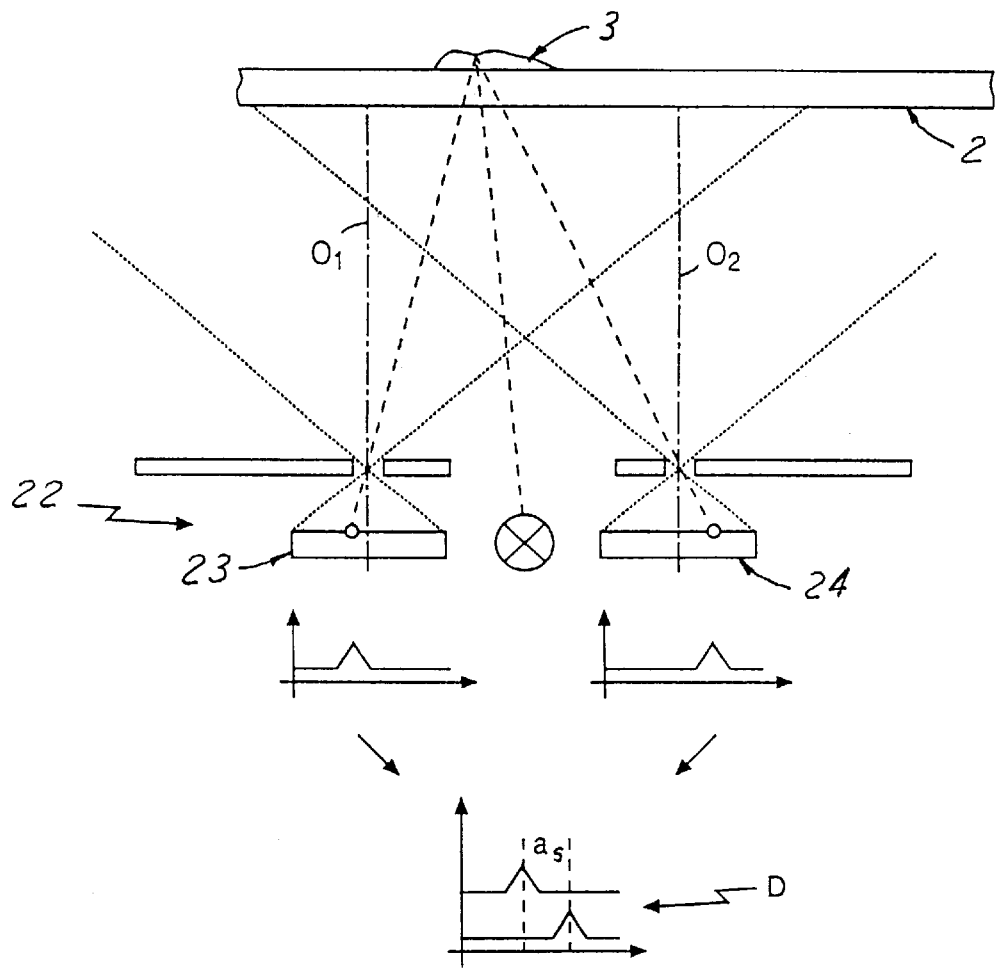
FIG. 3, a schematized representation of an additional device for detecting objects present on a transparent pane, using a stereoscopic sensor array arrangement.

FIG. 3 shows an additional recording unit 22, which consists of two camera sensors 23, 24. The two camera sensors 23, 24 also each comprise, like the optical sensor array of FIG. 1, an optical system as well as a preceding perforated diaphragm. The camera sensors 23, 24 are focused to infinity, with both the inner and the outer surface of the windshield 2 in the depth of focus range of the imaging. The optical axes of the two camera sensors $O_1$ and $O_2$ are positioned mutually parallel and spaced apart from one another. As also with the arrangement according to FIG. 1, an imaging of the light reflections produced by the raindrops 3 onto different pixels of the camera sensors 23 and 24 takes place with this recording unit 22. Background influences imaged in a greater distance as compared with the windshield 2, on the other hand, occupy pixels with the same position. Thus a disparity estimation is made to determine the depth. As previously described, the difference image formation is done starting from the two simultaneously recorded pane section images.

Figure 4:
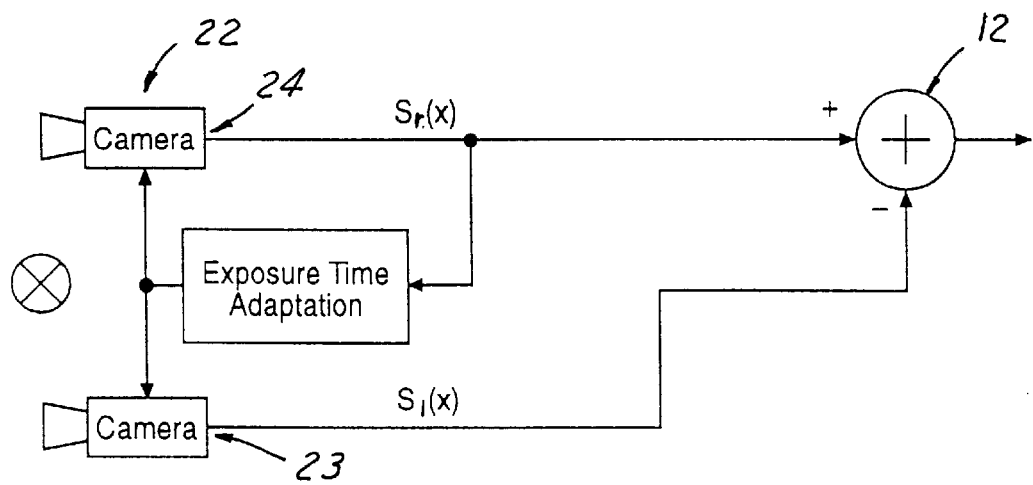
FIG. 4, a schematized block circuit diagram for acquiring a difference image for pane section images in keeping with the device described in FIG. 3.

FIG. 4 again shows the recording unit 22, of which the exposure time is controlled, in a schematized block circuit diagram. The outputs of the two camera sensors 23, 24 are applied directly to the difference image former 12. The additional analysis is done according to the analysis methods described for FIG. 2.

From the description of the invention, it becomes clear that by determining the difference image from two individual images, it is possible, for instance, for a rain sensor whose data are very reliable to be prepared. Both line and surface cameras can be used as optical sensor arrays. The stereoscopic arrangement of sensor arrays shown in FIGS. 3 and 4 can take on other monitoring functions in addition to a function as a recording unit 22 of a rain sensor.

From the description of the invention, it additionally becomes clear that the analysis of the pane section images can be done in software, instead of the analysis by means of circuit technology illustrated in the figures.

COLLECTION OF REFERENCE CHARACTERS

1 Recording unit
2 Windshield
3 Raindrop
4 Line sensor
5 Convex lens
6 Hole diaphragm
7 Illumination apparatus
8 IR diode
9 IR diode
10 Device for exposure time adaptation
11 Image memory
12 Difference image former
13 Edge operator element
14 Median filter
15 Low-pass filter operating in the time domain
16 Decider element
17 Image energy calculation element
18 Comparator element
19 Microprocessor
20 Cluster element
21 Statistical evaluation element
22 Recording unit
23 Camera sensor
24 Camera sensor
D Difference image
$O_1$ Optical axis
$O_1$[sic; $O_2$] Optical axis
$R_r$ Reflection for right-side illumination
$R_1$ Reflection for left-side illumination
$R_{r'}$ Reflection component for right-side illumination
$R_{l'}$ Reflection component for left-side illumination

What is claimed is:

1. A method for detecting the presence of objects on a windshield, the method comprising:

positioning an optical sensor array in optical communication with the windshield, the optical sensor array having an array of pixels for detecting light reflected from the windshield, each pixel having an individual position within the optical sensor array;

illuminating the windshield with light from a first light source positioned at a first angle of incidence with respect to the windshield and with light from a second light source positioned at a second angle of incidence with respect to the windshield;

detecting light reflected from the windshield onto pixels of the optical sensor array;

imaging the reflected light detected by the pixels of the optical sensor array to generate first and second images, wherein the first image is indicative of light from the first light source reflected by the windshield and detected by a first pixel at a first position in the optical sensor array, wherein the second image is indicative of light from the second light source reflected by the windshield and detected by a second pixel at a second position in the optical sensor array;

determining a difference image of the first and second images, the difference image being indicative of the pixels of the optical sensor array detecting light reflected by the windshield from the first and second light sources; and analyzing the difference image to determine the presence of objects on the windshield.

2. The method of claim 1 wherein:

analyzing the difference image includes using stochastic operators.

3. The method of claim 1 wherein:

analyzing the difference image includes using time-domain low-pass filtering.

4. The method of claim 1 wherein:

analyzing the difference image includes preparing a binary image of the first and second image pairs such that each pixel of the optical sensor array is assigned either the value of 0 or 1 depending on the whether the pixels detect light reflected from the windshield.

5. The method of claim 4 wherein:

analyzing the difference image includes clustering adjacent pixels with the value 1 and then performing a statistical analysis of the clusters.

6. The method of claim 1 wherein:

analyzing the difference image includes performing a total-image energy calculation in which values of the pixels of the difference image are summed, wherein the values being indicative of the reflected light detected by the pixels, and comparing the total-image energy calculation to a threshold value.

7. A method for detecting the presence of objects on a windshield, the method comprising:

positioning a first optical sensor array adjacent to the windshield at a first angle of incidence with respect to the windshield, the first optical sensor array having an array of pixels for detecting light reflected from the windshield, each pixel having an individual position within the first optical sensor array;

positioning a second optical sensor array adjacent to the windshield at a second angle of incidence with respect to the windshield, the second optical sensor array having an array of pixels for detecting light reflected from the windshield, each pixel having an individual position within the second optical sensor array;

illuminating the windshield with light from a light source;

detecting light reflected from the windshield onto pixels of the first and second optical sensor arrays;

imaging the reflected light detected by the pixels of the first and second optical sensor arrays to generate first and second images, wherein the first image is indicative of light from the light source reflected by the windshield and detected by a pixel at a first position in the first optical sensor array, wherein the second image is indicative of light from the second light source reflected by the windshield and detected by a pixel at a second position in the second optical sensor array;

determining a difference image of the first and second images, the difference image being indicative of the pixels of the first and second optical sensor arrays detecting light reflected by the windshield from the light source; and analyzing the difference image to determine the presence of objects on the windshield.

8. A device for detecting the presence of objects on a windshield, the device comprising:

a first light source positioned at a first angle of incidence with respect to the windshield for illuminating the windshield with light;

a second light source positioned at a second angle of incidence with respect to the windshield for illuminating the windshield with light;

an optical sensor array positioned adjacent to the windshield, the optical sensor array having an array of pixels for detecting light reflected from the windshield, each pixel having an individual position within the optical sensor array, the optical sensor array operable for imaging the reflected light detected by the pixels of the optical sensor array to generate first and second images, wherein the first image is indicative of light from the first light source reflected by the windshield and detected by a first pixel at a first position in the optical sensor array, wherein the second image is indicative of light from the second light source reflected by the windshield and detected by a second pixel at a second position in the optical sensor array;

an analysis unit for determining a difference image of the first and second images, the difference image being indicative of the pixels of the optical sensor array detecting light reflected by the windshield from the first and second light sources, wherein the analysis unit analyzes the difference image to determine the presence of objects on the windshield.

9. The device of claim 8 wherein:

the analysis unit analyzes the difference image includes using stochastic operators.

10. The device of claim 8 wherein:

the analysis unit analyzes the difference image includes using time-domain low-pass filtering.

11. The device of claim 8 wherein:

the analysis unit analyzes the difference image by preparing a binary image of the first and second image pairs such that each pixel of the optical sensor array is assigned either the value of 0 or 1 depending on the whether the pixels detect light reflected from the windshield.

12. The device of claim 5 wherein:

the analysis unit analyzes the difference image by clustering adjacent pixels with the value 1 and then performing a statistical analysis of the clusters.

13. The device of claim 5 wherein:

the analysis unit analyzes the difference image includes performing a total-image energy calculation in which values of the pixels of the difference image are summed up, wherein the values being indicative of the reflected light detected by the pixels, and comparing the total-image energy calculation to a threshold value.

* * * * *